United States Patent
Hinayama et al.

(10) Patent No.: US 12,403,449 B2
(45) Date of Patent: Sep. 2, 2025

(54) WATER-ABSORBING RESIN

(71) Applicants: SUMITOMO SEIKA CHEMICALS CO., LTD., Hyogo (JP); SUMITOMO SEIKA SINGAPORE PTE. LTD., Singapore (SG)

(72) Inventors: Tetsuhiro Hinayama, Himeji (JP); Sok Kiat Cheng, Singapore (SG)

(73) Assignees: SUMITOMO SEIKA CHEMICALS CO., LTD., Hyogo (JP); SUMITOMO SEIKA SINGAPORE PTE. LTD., Singapore (SG)

( * ) Notice: Subject to any disclaimer, the term of this patent is extended or adjusted under 35 U.S.C. 154(b) by 765 days.

(21) Appl. No.: 17/291,149

(22) PCT Filed: Oct. 31, 2019

(86) PCT No.: PCT/JP2019/042766
§ 371 (c)(1),
(2) Date: May 4, 2021

(87) PCT Pub. No.: WO2020/095811
PCT Pub. Date: May 14, 2020

(65) Prior Publication Data
US 2022/0126271 A1    Apr. 28, 2022

(30) Foreign Application Priority Data
Nov. 5, 2018    (JP) .................. 2018-208212

(51) Int. Cl.
*B01J 20/26* (2006.01)
*A61L 15/24* (2006.01)
*B01J 20/24* (2006.01)

(52) U.S. Cl.
CPC ............. *B01J 20/267* (2013.01); *A61L 15/24* (2013.01); *B01J 20/24* (2013.01)

(58) Field of Classification Search
CPC ...... B01J 20/267; B01J 20/24; B01J 2220/68; B01J 20/261; B01J 20/28011;
(Continued)

(56) References Cited

U.S. PATENT DOCUMENTS 5,180,798 A    1/1993  Nakamura et al.
2002/0040095 A1*  4/2002  Dairoku .................. A61L 15/24
                                                        524/832
(Continued)

FOREIGN PATENT DOCUMENTS

EP    1 637 105 A1    3/2006
EP    1 882 701 A1    1/2008
(Continued)

OTHER PUBLICATIONS

Extended European Search Report dated Jul. 13, 2022 from the European Patent Office in EP Application No. 19881530.0.
(Continued)

*Primary Examiner* — Andrew J. Oyer
(74) *Attorney, Agent, or Firm* — Sughrue Mion, PLLC

(57) ABSTRACT

A water-absorbent resin that can reduce the amount of backflow of an absorbed liquid even when the water-absorbent resin is used at a low content in an absorbent material is provided. An absorbent article comprising an absorbent material containing the resin is also provided. The resin is a crosslinked polymer of a water-soluble ethylenically unsaturated monomer and has a dry-up index of 1.85 or more, as represented by equation (1):

dry-up index=overall absorption capacity term
    α×water absorption rate term β    (1)

where the overall absorption capacity term α and the water absorption rate term β are determined according to equations (2) and (3):

(Continued)

$$\text{overall absorption capacity term } \alpha = \frac{\begin{pmatrix} \text{physiological saline absorption} \\ \text{capacity under a load of 2.07 kPa} - \\ \text{physiological saline absorption} \\ \text{capacity under a load of 4.82 kPa} \end{pmatrix}}{\begin{pmatrix} \text{physiological saline absorption capacity} - \\ \text{physiological saline retention capacity} \end{pmatrix}}; \qquad (2)$$

$$\text{water absorption rate term } \beta = \text{dynamic water absorption rate/static water absorption rate} \qquad (3).$$

7 Claims, 1 Drawing Sheet

(58) Field of Classification Search
CPC ........ A61L 15/24; A61L 15/60; C08F 220/06; C08F 20/06; C08J 3/075; C08J 2333/02; C08J 3/245; C08J 3/24; A61F 2013/530481; A61F 2013/530642; A61F 2013/530737; A61F 13/15203; A61F 13/53
See application file for complete search history.

(56) References Cited

U.S. PATENT DOCUMENTS

| | | |
|---|---|---|
| 2009/0281247 A1 | 11/2009 | Handa et al. |
| 2013/0130017 A1 | 5/2013 | Takatori et al. |
| 2013/0324396 A1* | 12/2013 | Honda ............... C08F 4/04 502/402 |
| 2017/0107312 A1 | 4/2017 | Hinayama et al. |
| 2017/0107313 A1* | 4/2017 | Murakami ........... C08F 2/20 |
| 2017/0203279 A1 | 7/2017 | Murakami et al. |

FOREIGN PATENT DOCUMENTS

| | | |
|---|---|---|
| EP | 2 993 189 A1 | 3/2016 |
| EP | 2 993 191 A1 | 3/2016 |
| EP | 3 153 529 A1 | 4/2017 |
| EP | 1 291 368 B1 | 5/2017 |
| EP | 2 993 190 B1 | 1/2018 |
| EP | 3778721 A1 | 2/2021 |
| JP | H3-227301 A | 10/1991 |
| JP | 2001-523733 A | 11/2001 |
| JP | 2006-176570 A | 7/2006 |
| JP | 2012-041419 A | 3/2012 |
| JP | 2012-144608 A | 8/2012 |
| JP | 2016-028115 A | 2/2016 |
| JP | 2016-028117 A | 2/2016 |
| WO | 99/25393 A2 | 5/1999 |
| WO | 2007/123188 A1 | 11/2007 |
| WO | 2012/023433 A1 | 2/2012 |
| WO | 2016/006132 A1 | 1/2016 |

OTHER PUBLICATIONS

A third party observation dated Feb. 22, 2021 filed against the corresponding International Application No. PCT/JP2019/042766.
International Search Report for PCT/JP2019/042766, dated Dec. 10, 2019.

* cited by examiner

WATER-ABSORBING RESIN

CROSS REFERENCE TO RELATED APPLICATIONS

This application is a National Stage of International Application No. PCT/JP2019/042766 filed Oct. 31, 2019, claiming priority based on Japanese Patent Application No. 2018-208212 filed Nov. 5, 2018.

TECHNICAL FIELD

The present disclosure relates to a water-absorbent resin, a method for producing the water-absorbent resin, and the like. More specifically, the present disclosure relates to a water-absorbent resin forming an absorbent material suitably used in an absorbent article for hygiene materials, such as sanitary products and disposable diapers, a method for producing the water-absorbent resin, and the like.

BACKGROUND ART

Absorbent articles for hygiene materials, such as sanitary products and disposable diapers, generally comprise an absorbent material that contains hydrophilic fibers and a water-absorbent resin as main constituents. Examples of known water-absorbent resins include hydrolysates of starch-acrylonitrile graft copolymers, neutralized products of starch-acrylic acid graft copolymers, saponified products of vinyl acetate-acrylic acid ester copolymers, partially neutralized polyacrylic acids, and the like.

In general, when the water-absorbent resin content in an absorbent material is low, the texture (softness) of the absorbent material is excellent, but the absorption properties typified by the amount of backflow are not satisfactory. Increasing the water-absorbent resin content tends to improve the absorption properties after absorption of body fluids etc., but impairs the texture of the absorbent material. Further, it is difficult to uniformly disperse a large amount of a water-absorbent resin in an absorbent material, and improvement in the properties due to the increased amount of a water-absorbent resin is not necessarily ensured. It is thus difficult to satisfy both absorption properties and texture in absorbent materials. Accordingly, there is a demand for a water-absorbent resin having the characteristics of enhancing the absorption properties in an absorbent material even when the water-absorbent resin content in the absorbent material is low.

Examples of characteristics of water-absorbent resins desired in order to enhance the absorption properties in absorbent articles for hygiene materials include high water retention capacity, high water absorption capacity under a load, and the like. Research has been conducted to obtain a water-absorbent resin having such characteristics. For example, the following proposals have been made. Specifically, a method for producing a water-absorbent resin having a large particle size, less fine powder, a sharp distribution, and excellent wettability by water in addition to excellent water absorption properties by performing reversed-phase suspension polymerization of a water-soluble ethylenically unsaturated monomer in multiple stages (see Patent Literature 1); a method for producing water-absorbent resin particles, the method comprising subjecting a water-soluble ethylenically unsaturated monomer to reversed-phase suspension polymerization to give primary particles having a specific median particle size and then performing a reversed-phase suspension polymerization reaction by adding a water-soluble ethylenically unsaturated monomer for the second stage to give secondary particles having a specific median particle size (see Patent Literature 2); a water-absorbent resin formed by agglomerating primary particles according to a reversed-phase suspension polymerization method, the primary particles being obtained by polymerizing a water-soluble ethylenically unsaturated monomer according to a reversed-phase suspension polymerization method, the primary particles having a median particle size of 100 to 250 µm, the water-absorbent resin having a physiological saline retention capacity of 30 g/g or less (see Patent Literature 3); and the like are known.

CITATION LIST

Patent Literature

PTL 1: JPH03-227301A
PTL 2: WO2007/123188
PTL 3: WO2012/023433

SUMMARY OF INVENTION

Technical Problem

A primary object of the present disclosure is to provide a water-absorbent resin that enables a reduction in the amount of backflow of an absorbed liquid from an absorbent material even when the water-absorbent resin content in the absorbent material is low.

Solution to Problem

The present inventors found the possibility that the use of a water-absorbent resin satisfying a specific index can reduce the amount of backflow of an absorbed liquid from an absorbent material even when the water-absorbent resin content in the absorbent material is low. The inventors further made improvements.

The present disclosure includes, for example, the subject matter described in the following items.

Item 1. A water-absorbent resin that is a crosslinked polymer of a water-soluble ethylenically unsaturated monomer, the water-absorbent resin having a dry-up index of 1.85 or more, the dry-up index being represented by the following equation (1):

$$\text{dry-up index} = \text{overall absorption capacity term } \alpha \times \text{water absorption rate term } \beta \quad (1)$$

wherein the overall absorption capacity term $\alpha$ and the water absorption rate term $\beta$ are determined according to the following equations (2) and (3):

$$\text{overall absorption capacity term } \alpha = \frac{\left(\begin{array}{c}\text{physiological saline absorption}\\\text{capacity under a load of 2.07 kPa} -\\\text{physiological saline absorption}\\\text{capacity under a load of 4.82 kPa}\end{array}\right)}{\left(\begin{array}{c}\text{physiological saline absorption capacity} -\\\text{physiological saline retention capacity}\end{array}\right)} \quad (2)$$

$$\text{water absorption rate term } \beta = \text{dynamic water absorption rate/static water absorption rate} \quad (3)$$

Item 2. The water-absorbent resin according to Item 1, wherein the overall absorption capacity term α is 0.95 or more.

Item 3. The water-absorbent resin according to Item 1 or 2, wherein the water absorption rate term β is 1.56 or more.

Item 4. The water-absorbent resin according to any one of Items 1 to 3, wherein the difference between the physiological saline absorption capacity and the physiological saline retention capacity is 18 or less.

Item 5. The water-absorbent resin according to any one of Items 1 to 4, wherein the difference between the physiological saline absorption capacity under a load of 2.07 kPa and the physiological saline absorption capacity under a load of 4.82 kPa is 17 to 36.

Item 6. An absorbent material comprising 5 to 50 mass % of the water-absorbent resin according to any one of Items 1 to 5 or any one of Items A to F below.

Item A.

A water-absorbent resin that is a crosslinked polymer of a water-soluble ethylenically unsaturated monomer, the water-absorbent resin being prepared by a polymerization method that satisfies at least two of the following conditions (i), (ii), and (iii):
(i) the molar ratio of a water-soluble ethylenically unsaturated monomer and an internal crosslinking agent used in polymerization in the first stage (water-soluble ethylenically unsaturated monomer/internal crosslinking agent) is $10 \times 10^3$ to $15 \times 10^3$;
(ii) the molar ratio of a water-soluble ethylenically unsaturated monomer and an internal crosslinking agent used in polymerization in the second stage (water-soluble ethylenically unsaturated monomer/internal crosslinking agent) is $15 \times 10^3$ to $25 \times 10^3$;
(iii) the molar ratio of the total amount of water-soluble ethylenically unsaturated monomer used in polymerization in which a resin used in a post-crosslinking reaction is prepared and a post-crosslinking agent (water-soluble ethylenically unsaturated monomer/post-crosslinking agent) is $2.5 \times 10^3$ to $4.5 \times 10^3$.

Item B.

The water-absorbent resin according to any one of Items 1 to 5, wherein the water-absorbent resin is prepared by a polymerization method that satisfies at least two of the following conditions (i), (ii), and (iii):
(i) the molar ratio of a water-soluble ethylenically unsaturated monomer and an internal crosslinking agent used in polymerization in the first stage (water-soluble ethylenically unsaturated monomer/internal crosslinking agent) is $10 \times 10^3$ to $15 \times 10^3$;
(ii) the molar ratio of a water-soluble ethylenically unsaturated monomer and an internal crosslinking agent used in polymerization in the second stage (water-soluble ethylenically unsaturated monomer/internal crosslinking agent) is $15 \times 10^3$ to $25 \times 10^3$;
(iii) the molar ratio of the total amount of water-soluble ethylenically unsaturated monomer used in polymerization in which a resin used in a post-crosslinking reaction is prepared and a post-crosslinking agent (water-soluble ethylenically unsaturated monomer/post-crosslinking agent) is $2.5 \times 10^3$ to $4.5 \times 10^3$.

Item C.

The water-absorbent resin according to Item A or B, wherein the water-soluble ethylenically unsaturated monomer is (meth)acrylic acid.

Item D.

The water-absorbent resin according to any one of Items A to C, wherein at least one of conditions (i) and (ii) is satisfied, and the internal crosslinking agent is at least one member selected from the group consisting of (poly)ethylene glycol diglycidyl ether, (poly)propylene glycol diglycidyl ether, and (poly)glycerol diglycidyl ether.

Item E.

The water-absorbent resin according to any one of Items A to C, wherein at least condition (iii) is satisfied, and the post-crosslinking agent is at least one member selected from the group consisting of (poly)ethylene glycol diglycidyl ether, (poly)propylene glycol diglycidyl ether, and (poly)glycerol diglycidyl ether.

Item F.

The water-absorbent resin according to any one of Items A to E, wherein the polymerization method that satisfies at least two of conditions (i), (ii), and (iii) is reversed-phase suspension polymerization (preferably one-stage or two-stage reversed-phase suspension polymerization, more preferably two-stage reversed-phase suspension polymerization).

Item G.

The water-absorbent resin according to any one of Items A to F, wherein the polymerization method is a polymerization method that satisfies all of conditions (i), (ii), and (iii).

Advantageous Effects of Invention

Provided are a water-absorbent resin that enables a reduction in the amount of backflow in an absorbent material even when the water-absorbent resin is used at a low content in the absorbent material, a method for producing the water-absorbent resin, and the like.

DESCRIPTION OF EMBODIMENTS

Embodiments encompassed by the present disclosure are described in more detail below. The present disclosure preferably includes a specific water-absorbent resin, a method for producing the water-absorbent resin, and the like, but is not limited thereto. The present disclosure includes everything disclosed in the present specification and recognizable to those skilled in the art.

1. Water-Absorbent Resin

The water-absorbent resin encompassed by the present disclosure is a water-absorbent resin that is formed from a polymer of a water-soluble ethylenically unsaturated monomer, wherein the dry-up index represented by the following equation (1), which is the product of overall absorption capacity term α and water absorption rate term β, is 1.85 or more. This water-absorbent resin may be referred to as "the water-absorbent resin according to the present disclosure."

$$\text{Dry-up index} = \text{overall absorption capacity term } \alpha \times \text{water absorption rate term } \beta \quad (1)$$

The water-absorbent resin according to the present disclosure preferably has a dry-up index of 1.9 to 5.0. The lower limit of the numerical range may be, for example, 2.0, 2.1, 2.2, 2.3, 2.4, 2.5, 2.6, 2.7, 2.8, or 2.9. The upper limit of the numerical range may be, for example, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, or 3.0. The numerical range is more preferably, for example, 2.0 to 4.0, and even more preferably 2.1 to 3.0.

The overall absorption capacity term α of the water-absorbent resin is a value calculated according to the following equation (2).

$$\text{Overall absorption capacity term } \alpha = \frac{\begin{pmatrix} \text{physiological saline absorption} \\ \text{capacity under a load of 2.07 kPa} - \\ \text{physiological saline absorption} \\ \text{capacity under a load of 4.82 kPa} \end{pmatrix}}{\begin{pmatrix} \text{physiological saline absorption capacity} - \\ \text{physiological saline retention capacity} \end{pmatrix}} \quad (2)$$

In the present specification, the "physiological saline absorption capacity" is a value determined as below. That is, while stirring 500 g of physiological saline at 600 r/min, 2.0 g of a water-absorbent resin is added thereto, and stirring is performed for 60 minutes. The resulting mixture is then filtered through a standard sieve having an opening of 75 μm. The sieve is inclined at an angle of about 30 degrees relative to the horizon, and left to stand in this state for 30 minutes. Thereafter, the mass of the swelled gel is measured, thereby determining the physiological saline absorption capacity.

In the present specification, the "physiological saline retention capacity" is a value determined as below. That is, while stirring 500 g of physiological saline at 600 r/min, 2.0 g of a water-absorbent resin is added thereto, and stirring is performed for 30 minutes. The resulting mixture is then poured into a cotton bag (cotton broadcloth No. 60), and the cotton bag is dehydrated for 1 minute with a dehydrator with the centrifugal force set to 167 G. The mass of the swelled gel after dehydration is measured, thereby determining the physiological saline retention capacity.

In the present specification, the "physiological saline absorption capacity under a load of 2.07 kPa" is determined as below. That is, 0.1 g of a water-absorbent resin is homogeneously sprinkled in a cylinder having an inner diameter of 2.0 cm in which a nylon mesh (200 mesh) is placed. The water-absorbent resin is allowed to absorb water with a load of 2.07 kPa uniformly applied to the water-absorbent resin using a weight. The amount of physiological saline 60 minutes after the start of absorption is measured, thereby determining the physiological saline absorption capacity under a load of 2.07 kPa. For the measurement, a measurement device X schematically shown in FIG. 1 can be suitably used.

As described above, in the present specification, the terms "physiological saline absorption capacity" and "physiological saline absorption capacity under a load of 2.07 kPa" are clearly distinguished from each other.

In the present specification, the "physiological saline absorption capacity under a load of 4.82 kPa" is determined as below. That is, 0.9 g of a water-absorbent resin is added to a supporting cylinder having an inner diameter of 60 mm in which a wire mesh (400 mesh) is placed. The water-absorbent resin is allowed to absorb water with a load of 4.82 kPa uniformly applied to the water-absorbent resin using a weight. The amount of physiological saline 60 minutes after the start of absorption is measured, thereby determining the physiological saline absorption capacity under a load of 4.82 kPa. For the measurement, a measurement device Y schematically shown in FIG. 2 can be suitably used.

As described above, in the present specification, the terms "physiological saline absorption capacity" and "physiological saline absorption capacity under a load of 4.82 kPa" are clearly distinguished from each other.

In the water-absorbent resin according to the present disclosure, the overall absorption capacity term α is preferably 0.95 or more, more preferably 1.00 to 4.00, and even more preferably 1.05 to 2.00. The upper limit may be 4.00, 3.00, 2.00, 1.80, 1.65, or 1.55.

In the water-absorbent resin according to the present disclosure, the difference between the physiological saline absorption capacity and the physiological saline retention capacity is preferably 18 or less, more preferably 17 or less, and even more preferably 16 or less. The difference between the physiological saline absorption capacity and the physiological saline retention capacity is also preferably 5 or more, more preferably 8 or more, and even more preferably 10 or more.

In the water-absorbent resin according to the present disclosure, the difference between the physiological saline absorption capacity under a load of 2.07 kPa and the physiological saline absorption capacity under a load of 4.82 kPa is preferably 17 to 36, more preferably 17 to 33, and even more preferably 17 to 30.

The water absorption rate term β of the water-absorbent resin is expressed as the ratio of the dynamic water absorption rate to the static water absorption rate, and is calculated according to the following equation (3).

$$\text{Water absorption rate term } \beta = \text{dynamic water absorption rate/static water absorption rate} \quad (3)$$

The dynamic water absorption rate is determined as below. That is, 50 g of physiological saline at a temperature of 25° C. is stirred with a magnetic stirrer bar (8-mm diameter×30 mm) to generate a vortex at a rotation frequency of 600 r/min. Then, 2.0 g of a water-absorbent resin is added at a time, and the time from the addition of the water-absorbent resin to the point at which the vortex on the liquid surface disappears is measured, thereby determining the dynamic water absorption rate. More specifically, the dynamic water absorption rate is a value measured by the method in the Examples described later.

The static water absorption rate is determined as below. That is, 0.1 g of a water-absorbent resin is homogeneously sprinkled in a cylinder having an inner diameter of 2.0 cm in which a nylon mesh (200 mesh) is placed. The amount of physiological saline absorbed by the water-absorbent resin is measured without applying a load to the water-absorbent resin using a weight. The time (seconds) required for the water-absorbent resin to absorb 25 g of physiological saline per 1 g of the water-absorbent resin is measured, thereby determining the static water absorption rate. More specifically, the static water absorption rate is a value measured by the method in the Examples described later. For the measurement, the measurement device X schematically shown in FIG. 1 can be suitably used.

In the water-absorbent resin according to the present disclosure, the water absorption rate term R is preferably 1.56 or more, more preferably 1.60 or more, and even more preferably 1.65 or more. The upper limit is not particularly limited. The upper limit is preferably 3 or less and may be 2.95, 2.9, 2.85, 2.8, 2.75, or 2.7 or less.

In order to reduce foreign-body sensation when sanitary products, disposable diapers, and like hygiene materials containing the water-absorbent resin are worn, the water-absorbent resin according to the present disclosure preferably has a median particle size of 200 to 600 μm, more preferably 250 to 550 μm, and even more preferably 300 to 500 μm.

Additives according to the purpose may be added to the resulting water-absorbent resin. Such additives include inorganic powders, surfactants, oxidants, reducing agents, metal chelating agents, radical chain inhibitors, antioxidants, antimicrobial agents, deodorants, and the like. For example, 0.05 to 5 parts by mass of amorphous silica (inorganic powder) per 100 parts by mass of the water-absorbent resin may be added to improve the fluidity of the water-absorbent resin.

2. Method for Producing Water-Absorbent Resin

Examples of the method for obtaining the water-absorbent resin according to the present disclosure include a reversed-phase suspension polymerization method, an aqueous solution polymerization method, and the like. As an example of the method for producing the water-absorbent resin according to the present disclosure, a reversed-phase suspension polymerization method is described in more detail below.

2-1. Polymerization Step

Polymerization can be performed by a method known in the field of water-absorbent resin preparation or a method conceivable from a known method. Among these, reversed-phase suspension polymerization is preferable. In the reversed-phase suspension polymerization method, polymerization is performed by stirring and mixing, and heating a water-soluble ethylenically unsaturated monomer aqueous solution containing a radical polymerization initiator and, if necessary, a crosslinking agent (internal crosslinking agent), in a hydrocarbon dispersion medium in the presence of a dispersion stabilizer.

The polymerization reaction may be performed in one stage, or in multiple stages such as two or more stages. When the polymerization reaction is performed in multiple stages, the number of stages is preferably two or three from the standpoint of increasing productivity. When the polymerization reaction is performed in multiple stages, the polymerization in the first stage may be performed by the method described later, and then a water-soluble ethylenically unsaturated monomer aqueous solution may be added to and mixed with the reaction mixture obtained in the polymerization reaction in the first stage, followed by performing the polymerization in the second stage in the same manner as in the first stage. Further, the multistage polymerization can be performed by repeating the same operation. Moreover, when the polymerization is performed in two or more stages, the same or different polymerization methods may be used, and it is more preferable to use the same polymerization method. It is even more preferable to use a reversed-phase suspension polymerization method in the polymerization in each stage.

In the polymerization in each of the second and subsequent stages, for example, a radical polymerization initiator and an internal crosslinking agent, in addition to a water-soluble ethylenically unsaturated monomer, may be added in a molar ratio of each component to the water-soluble ethylenically unsaturated monomer within the numerical ranges described later, based on the amount of the water-soluble ethylenically unsaturated monomer added in the polymerization in each of the second and subsequent stages, and then polymerization may be performed.

Water-Soluble Ethylenically Unsaturated Monomer

Examples of the water-soluble ethylenically unsaturated monomer include (meth)acrylic acid (in this specification, "acrylic" and "methacrylic" are together referred to as "(meth)acrylic"; the same applies below) and salts thereof; 2-(meth)acrylamide-2-methylpropanesulfonic acid and salts thereof; nonionic monomers, such as (meth)acrylamide, N,N-dimethyl (meth)acrylamide, 2-hydroxyethyl (meth) acrylate, N-methylol (meth)acrylamide, and polyethylene glycol mono(meth) acrylate; amino group-containing unsaturated monomers, such as N,N-diethylaminoethyl (meth)acrylate, N,N-diethylaminopropyl (meth)acrylate, and diethylaminopropyl (meth)acrylamide, and quaternized products thereof; and the like. These water-soluble ethylenically unsaturated monomers may be used singly or in a combination of two or more. In particular, from the standpoint of convenience in industrial availability, (meth)acrylic acid and salts thereof, (meth)acrylamide, and N,N-dimethyl acrylamide are preferable, and (meth)acrylic acid and salts thereof are more preferable. Of these, for example, acrylic acid and salts thereof are widely used as raw materials for water-absorbent resins. Acrylic acid and/or a salt thereof may be copolymerized with one or more other water-soluble ethylenically unsaturated monomers described above, and the resulting copolymer may be used. In this case, it is preferable to use 70 to 100 mol % of acrylic acid and/or a salt thereof as the main water-soluble ethylenically unsaturated monomer of the total water-soluble ethylenically unsaturated monomers.

When the water-soluble ethylenically unsaturated monomer described above is subjected to reversed-phase suspension polymerization, the monomer for use may be prepared in the form of an aqueous solution in order to improve the dispersibility in a hydrocarbon dispersion medium. The concentration of the water-soluble ethylenically unsaturated monomer in such an aqueous solution may be typically 20 mass % to the saturated concentration. In order to increase the water absorption properties of the resulting water-absorbent resin while ensuring productivity, the concentration of the water-soluble ethylenically unsaturated monomer is preferably 20 to 50 mass %, more preferably 22 to 45 mass %, and even more preferably 24 to 36 mass %.

When the water-soluble ethylenically unsaturated monomer has an acid group, like (meth)acrylic acid or 2-(meth) acrylamide-2-methylpropanesulfonic acid, the acid group of the water-soluble ethylenically unsaturated monomer for use may be neutralized with an alkaline neutralizer beforehand as necessary. Examples of alkaline neutralizers include alkali metal salts, such as sodium hydroxide, sodium carbonate, sodium hydrogen carbonate, potassium hydroxide, and potassium carbonate; ammonia; and the like. In particular, these alkaline neutralizers may be prepared in the form of an aqueous solution in order to simplify the neutralization operation.

These alkaline neutralizers may be used singly or in a combination of two or more. In order to increase the water absorption properties by increasing the osmotic pressure of the resulting water-absorbent resin and to avoid safety problems that may arise due to the presence of excessive alkaline neutralizer, the degree of neutralization of the water-soluble ethylenically unsaturated monomer with an alkaline neutralizer is preferably 40 to 90 mol %, more preferably 70 to 88 mol %, even more preferably 75 to 85 mol %, and still even more preferably 77 to 80 mol % of all acid groups in the water-soluble ethylenically unsaturated monomer.

Hydrocarbon Dispersion Medium

Examples of hydrocarbon dispersion media include aliphatic hydrocarbons having 6 to 8 carbon atoms, such as n-hexane, n-heptane, 2-methylhexane, 3-methylhexane, 2,3- dimethylpentane, 3-ethylpentane, and n-octane; alicyclic hydrocarbons, such as cyclohexane, methylcyclohexane, cyclopentane, methylcyclopentane, trans-, 2-dimethylcyclopentane, cis-1,3-dimethylcyclopentane, and trans-1,3-dimethylcyclopentane; aromatic hydrocarbons, such as benzene, toluene, and xylene; and the like. These hydrocarbon dispersion media may be used singly or in a combination of two or more. Of these hydrocarbon dispersion media, from the standpoint of convenience in industrial availability, quality stability, and low price, n-hexane, n-heptane, and cyclohexane are preferably used. Examples of a mixture of hydrocarbon dispersion media described above include commercially available Exxsol Heptane (Exxon Mobil Corporation; containing 75 to 85 mass % of hydrocarbons, i.e., heptane and its isomer). Such a commercially available product may be used.

The amount of the hydrocarbon dispersion medium for use is typically preferably 80 to 1500 parts by mass, and more preferably 120 to 1200 parts by mass, per 100 parts by mass of the water-soluble ethylenically unsaturated monomer in the first stage, in order to uniformly disperse the water-soluble ethylenically unsaturated monomer aqueous solution and to facilitate control of the polymerization temperature.

Dispersion Stabilizer

The dispersion stabilizer may be a surfactant. Examples include sucrose fatty acid esters, polyglycerol fatty acid esters, sorbitan fatty acid esters, polyoxyethylene sorbitan fatty acid esters, polyoxyethylene glycerol fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, polyethylene glycol fatty acid esters, alkyl glucoside, N-alkyl gluconamide, polyoxyethylene fatty acid amide, polyoxyethylene alkylamine, and the like. Of these, from the standpoint of dispersion stability of the monomer aqueous solution, for example, sorbitol fatty acid esters, polyglycerol fatty acid esters, and sucrose fatty acid esters are preferable. These surfactants may be used singly or in a combination of two or more.

The amount of the surfactant for use is preferably 0.05 to 30 parts by mass, and more preferably 0.1 to 20 parts by mass, per 100 parts by mass of the water-soluble ethylenically unsaturated monomer used for polymerization, in order to keep the monomer aqueous solution well dispersed in a hydrocarbon dispersion medium and to achieve a dispersion effect that matches the amount of the used surfactant.

The dispersion stabilizer may be also a combination of a surfactant and a polymeric dispersant. Examples of usable polymeric dispersants include maleic anhydride-modified polyethylene, maleic anhydride-modified polypropylene, maleic anhydride-modified ethylene-propylene copolymers, maleic anhydride-modified EPDM (ethylene-propylene-diene terpolymer), maleic anhydride-modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, ethyl hydroxyethyl cellulose, and the like. These polymeric dispersants may be used singly or in a combination of two or more.

The amount of the polymeric dispersant for use is preferably 0.05 to 30 parts by mass, and more preferably 0.1 to 20 parts by mass, per 100 parts by mass of the water-soluble ethylenically unsaturated monomer used for polymerization, in order to keep the monomer aqueous solution well dispersed in a hydrocarbon dispersion medium and to achieve a dispersion effect that matches the amount of the used polymeric dispersant.

The timing for adding the surfactant used as a dispersion stabilizer may be before or after the addition of the monomer aqueous solution as long as it is before the start of the polymerization reaction. In particular, from the standpoint of reducing the amount of the hydrocarbon dispersion medium remaining in the resulting water-absorbent resin, it is preferable to disperse the monomer aqueous solution and then further disperse the surfactant before performing polymerization. The timing for adding the polymeric dispersant used in combination with the surfactant as a dispersion stabilizer may be before or after the addition of the monomer aqueous solution. From the standpoint of the dispersion stability of the monomer aqueous solution and a reduction in the amount of the hydrocarbon dispersion medium remaining in the water-absorbent resin, it is preferable to add the polymeric dispersant before dispersing the monomer aqueous solution. Specifically, it is more preferable to disperse the monomer aqueous solution in the hydrocarbon dispersion medium in which the polymeric dispersant is dispersed and then further disperse the surfactant before performing polymerization.

Radical Polymerization Initiator

Examples of radical polymerization initiators include persulfates, such as potassium persulfate, ammonium persulfate, and sodium persulfate; peroxides, such as methyl ethyl ketone peroxide, methyl isobutyl ketone peroxide, di-t-butyl peroxide, t-butyl cumyl peroxide, t-butyl peroxyacetate, t-butylperoxy isobutyrate, t-butylperoxy pivalate, and hydrogen peroxide; azo compounds, such as 2,2'-azobis (2-amidinopropane)dihydrochloride, 2,2'-azobis[2-(N-phenyl amidino)propane]dihydrochloride, 2,2'-azobis[2-(N-allyl amidino)propane]dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanovaleric acid); and the like. Of these radical polymerization initiators, potassium persulfate, ammonium persulfate, sodium persulfate, and 2,2'-azobis(2-amidinopropane)dihydrochloride are preferable from the standpoint of availability and easy handling. These radical polymerization initiators may be used singly or in a combination of two or more.

The amount of the radical polymerization initiator for use is typically preferably 0.005 to 1 mole, more preferably 0.01 to 0.5 moles, even more preferably 0.0125 to 0.1 moles, and still even more preferably 0.015 to 0.05 moles, per 100 moles of the water-soluble ethylenically unsaturated monomer used for polymerization, in order to avoid rapid polymerization reaction and to reduce the polymerization reaction time.

The reaction temperature for the polymerization reaction depends on the radical polymerization initiator used. The reaction temperature is typically preferably 20 to 110° C., and more preferably 40 to 90° C., in order to increase productivity by allowing prompt progress of polymerization and to remove polymerization heat more smoothly. The reaction time is typically preferably about 0.1 to 4 hours.

Internal Crosslinking Agent

When the water-soluble ethylenically unsaturated monomer is polymerized, a crosslinking agent may be used as necessary. When the polymerization is performed in multiple stages, a crosslinking agent may be used in all of the stages, or there may be one or more stages in which a crosslinking agent is not used. When the polymerization is performed in multiple stages, the types of the crosslinking agents used in the individual stages may be the same or different and are preferably the same. Examples of the crosslinking agent (hereinafter referred to as "internal crosslinking agent") include unsaturated polyesters obtained by reacting a polyol, such as a diol or a triol including (poly)ethylene glycol ("(poly)" refers to both cases with and without a prefix "poly;" the same applies below), (poly)propylene glycol, 1,4-butanediol, trimethylolpropane, or (poly)glycerol, with an unsaturated acid, such as (meth)acrylic acid, maleic acid, or fumaric acid; bisacrylamides, such as N,N-methylenebisacrylamide; di- or tri(meth)acrylic acid esters obtained by reacting a polyepoxide with (meth)acrylic acid; di(meth)acrylic acid carbamyl esters obtained by reacting a polyisocyanate, such as tolylene diisocyanate or hexamethylene diisocyanate, with (meth)acrylic acid hydroxyethyl; compounds having two or more polymerizable unsaturated groups, such as allylated starch, allylated cellulose, diallyl phthalate, N,N',N'-triallyl isocyanurate, and divinylbenzene; polyglycidyl compounds, such as diglycidyl compounds including (poly)ethylene glycol diglycidyl ether, (poly)propylene glycol diglycidyl ether, and (poly)glycerol diglycidyl ether, and triglycidyl compounds; epihalohydrin compounds, such as epichlorohydrin, epibromohydrin, and α-methyl epichlorohydrin; compounds having two or more reactive functional groups, such as isocyanate compounds including 2,4-tolylene diisocyanate and hexamethylene diisocyanate; and the like. Of these internal crosslinking agents, for example, polyglycidyl compounds are preferable, diglycidyl ether compounds are more preferable, and (poly)ethylene glycol diglycidyl ether is particularly preferable. These internal crosslinking agents may be used singly or in a combination of two or more. It is preferable that the internal crosslinking agent is added to the monomer aqueous solution and used.

When the internal crosslinking agent is used, the amount of the agent is preferably 0.00001 to 1 mole, and more preferably 0.0001 to 0.5 moles, per 100 moles of the water-soluble ethylenically unsaturated monomer, in order to sufficiently enhance the water absorption properties of the resulting water-absorbent resin.

Other Components

In an example of the method for producing the water-absorbent resin, when reversed-phase suspension polymerization is performed, other components may be added to the water-soluble ethylenically unsaturated monomer aqueous solution. Various additives, such as thickening agents and chain transfer agents, can be added as other components.

Thickening Agent

When the polymerization reaction is performed, a thickening agent may be added to the water-soluble ethylenically unsaturated monomer aqueous solution. The median particle size of the resulting water-absorbent resin can be controlled by adding a thickening agent to adjust the the aqueous solution viscosity.

Examples of thickening agents include hydroxyethyl cellulose, hydroxypropyl cellulose, methylcellulose, carboxy methylcellulose, polyacrylic acid, (partially) neutralized polyacrylic acid, polyethylene glycol, polyacrylamide, polyethyleneimine, dextrin, sodium alginate, polyvinyl alcohol, polyvinylpyrrolidone, polyethylene oxide, and the like. If the stirring rate during polymerization is the same, the higher the viscosity of the water-soluble ethylenically unsaturated monomer aqueous solution, the larger the median particle size of the resulting particles tends to be.

2-2. Post-Crosslinking Step

After the polymerization step, the water containing-gel (the water-absorbent resin that is obtained by the polymerization and contains water) can be subjected to a post-crosslinking reaction to increase the crosslink density near the surface of the water-absorbent resin, thereby enhancing various properties such as water absorption capacity under a load. In the production of the water-absorbent resin according to the present disclosure, post-crosslinking may be performed using a post-crosslinking agent.

Examples of post-crosslinking agents include those that can react with a carboxyl group in the water-absorbent resin. Typical examples of post-crosslinking agents include polyols, such as (poly)ethylene glycol, (poly)propylene glycol, 1,4-butanediol, trimethylolpropane, and (poly)glycerol; diglycidyl ether compounds, such as (poly)ethylene glycol diglycidyl ether, (poly)propylene glycol diglycidyl ether, and (poly)glycerol diglycidyl ether; epihalohydrin compounds, such as epichlorohydrin, epibromohydrin, and α-methylepichlorohydrin; compounds having two or more reactive functional groups, such as isocyanate compounds including 2,4-tolylene diisocyanate and hexamethylene diisocyanate; and the like. Of these, (poly)ethylene glycol diglycidyl ether is preferable. These may be used singly or in a combination of two or more. Further, the post-crosslinking agent may be dissolved in water, an organic solvent, or the like for use.

The amount of the post-crosslinking agent cannot be generally specified because it varies depending on the type of post-crosslinking agent. However, when the amount of the post-crosslinking agent is too small, the crosslink density of the surface layer of the water-absorbent resin tends to be insufficient, resulting in low water absorption capacity under a load. When the amount of the post-crosslinking agent is too large, the water retention capacity of the water-absorbent resin tends to decrease. Accordingly, the amount of the post-crosslinking agent for use is typically 0.00001 to 0.01 moles, preferably 0.00005 to 0.005 moles, and more preferably 0.0001 to 0.002 moles, per mole of the total amount of water-soluble ethylenically unsaturated monomer used for polymerization.

Regarding the timing for adding the post-crosslinking agent, the post-crosslinking agent is preferably added in a system in which water is present in an amount of 1 to 400 parts by mass, more preferably 5 to 200 parts by mass, and even more preferably 10 to 100 parts by mass, per 100 parts by mass of the total amount of water-soluble ethylenically unsaturated monomer. The amount of water means the total amount of water contained in the reaction system and water used as necessary when the post-crosslinking agent is added.

The reaction temperature in the post-crosslinking reaction is preferably 50 to 250° C., and more preferably 60 to 180° C. The reaction time for the post-crosslinking varies depending on the reaction temperature, type and amount of the post-crosslinking agent, etc. and thus cannot be generalized. The reaction time for the post-crosslinking is typically 1 to 300 minutes, and preferably 5 to 200 minutes.

2-3. Drying Step

The method may comprise a drying step of externally applying energy such as heat to the water containing-gel to remove water, the hydrocarbon dispersion medium, and the like by distillation. For example, in the case of removing water from the water containing-gel after reversed-phase suspension polymerization, the system in which the water containing-gel is dispersed in the hydrocarbon dispersion medium is heated to distill water and the hydrocarbon dispersion medium out of the system by azeotropic distillation. In this case, it is possible to perform continuous azeotropic distillation by recycling into the system only the hydrocarbon dispersion medium that has been distilled off. This technique is preferable from the viewpoints that the temperature in the system can be maintained at a temperature not higher than the azeotropic temperature and that the resin is less likely to deteriorate. Water and the hydrocarbon dispersion medium are distilled off to obtain particles of the water-absorbent resin.

In the drying step, the drying treatment may be performed under ordinary pressure or under reduced pressure. In order to increase drying efficiency, the drying treatment may be performed under a nitrogen stream or the like. When the drying treatment is performed under ordinary pressure, the drying temperature is preferably 70 to 250° C., and more preferably 80 to 180° C. When the drying treatment is performed under reduced pressure, the drying temperature is preferably 40 to 160° C., and more preferably 50 to 110° C.

A particularly preferable embodiment of the water-absorbent resin according to the present disclosure is a water-absorbent resin produced through a polymerization reaction of a water-soluble ethylenically unsaturated monomer. The water-absorbent resin is, for example, a water-absorbent resin satisfying at least two of the following three conditions (i) to (iii), and is more preferably a water-absorbent resin satisfying all of the three conditions.

(i) The molar ratio of a water-soluble ethylenically unsaturated monomer and an internal crosslinking agent used in the polymerization in the first stage (water-soluble ethylenically unsaturated monomer/internal crosslinking agent) is $10\times10^3$ to $15\times10^3$.

(ii) The molar ratio of a water-soluble ethylenically unsaturated monomer and an internal crosslinking agent used in the polymerization in the second stage (water-soluble ethylenically unsaturated monomer/internal crosslinking agent) is $15\times10^3$ to $25\times10^3$.

(iii) The molar ratio of the total amount of water-soluble ethylenically unsaturated monomer used in polymerization in which a resin used in a post-crosslinking reaction is prepared and a post-crosslinking agent (water-soluble ethylenically unsaturated monomer/post-crosslinking agent) is $2.5\times10^2$ to $4.5\times10^3$.

A water-absorbent resin that exhibits the above preferred overall absorption capacity term $\alpha$ and water absorption rate term $\beta$, and preferred dry-up index, can be prepared by preparing the water-absorbent resin so that at least two of these conditions or the three conditions are satisfied. In other words, the water-absorbent resin according to the present disclosure can be preferably prepared using these conditions (i) to (iii) as indices.

In condition (i), the molar ratio of a water-soluble ethylenically unsaturated monomer and an internal crosslinking agent used in the polymerization in the first stage (water-soluble ethylenically unsaturated monomer/internal crosslinking agent) is more preferably $10\times10^3$ to $14\times10^3$, even more preferably $10\times10^3$ to $13\times10^3$, and still even more preferably $11\times10^3$ to $12\times10^3$.

In condition (ii), the molar ratio of a water-soluble ethylenically unsaturated monomer and an internal crosslinking agent used in the polymerization in the second stage (water-soluble ethylenically unsaturated monomer/internal crosslinking agent) is more preferably $17.5\times10^3$ to $24\times10^3$, even more preferably $20\times10^3$ to $23\times10^3$, and still even more preferably $21\times10^3$ to $22\times10^3$.

In condition (iii), the molar ratio of the total amount of water-soluble ethylenically unsaturated monomer used in polymerization in which a resin used in a post-crosslinking reaction is prepared and a post-crosslinking agent (water-soluble ethylenically unsaturated monomer/post-crosslinking agent) is more preferably $3\times10^3$ to $4\times10^3$, and even more preferably $3\times10^3$ to $3.5\times10^3$.

The present disclosure also preferably encompasses a method for producing a water-absorbent resin so as to satisfy these conditions.

3. Absorbent Material and Absorbent Article

The water-absorbent resin according to the present disclosure is, for example, used with hydrophilic fibers to form an absorbent material. The absorbent material is suitably used in an absorbent article used for hygiene materials, such as sanitary products and disposable diapers.

The absorbent material comprises, for example, the water-absorbent resin and hydrophilic fibers. Examples of the structure of the absorbent material include a mixture dispersion obtained by mixing the water-absorbent resin and hydrophilic fibers so as to form a homogeneous composition; a sandwich structure in which the water-absorbent resin is sandwiched between the layers of hydrophilic fibers; a structure in which the water-absorbent resin and hydrophilic fibers are wrapped with tissue or the like; and the like. Other components, such as an adhesive binder for increasing the shape retention properties of the absorbent material (e.g., thermally adhesive synthetic fibers, a hot-melt adhesive, and an adhesive emulsion) may be added to the absorbent material.

The content of the water-absorbent resin according to the present disclosure in the absorbent material is preferably 5 to 50 mass %, more preferably 10 to 45 mass %, and even more preferably 15 to 40 mass-, of the total mass of the absorbent material.

Examples of hydrophilic fibers include cellulose fibers, such as cotton-like pulp obtained from wood, mechanical pulp, chemical pulp, and semi-chemical pulp; artificial cellulose fibers, such as rayon and acetate; fibers composed of synthetic resins, such as hydrophilized polyamide, polyester, and polyolefin; and the like.

The absorbent article can be prepared by holding the absorbent material between a liquid-permeable sheet (top sheet) through which liquid can permeate and a liquid-impermeable sheet (back sheet) through which liquid cannot permeate. The liquid-permeable sheet is disposed on the side that comes into contact with the body, and the liquid-impermeable sheet is disposed on the side opposite the side that comes into contact with the body.

Examples of the liquid-permeable sheet include air-through, spun-bonded, chemical-bonded, or needle-punched non-woven fabrics and porous synthetic resin sheets that are formed of fibers, such as polyethylene, polypropylene, or polyester. Examples of the liquid-impermeable sheet include synthetic resin films composed of resin, such as polyethylene, polypropylene, or polyvinyl chloride.

In the present specification, the term "comprising" includes "consisting essentially of" and "consisting of." Further, the present disclosure includes all of any combinations of the constituent requirements described in the present specification.

In addition, the various characteristics (properties, structures, functions, etc.) described in each embodiment of the present disclosure described above may be combined in any way in specifying the subjects included in the present disclosure. In other words, the present disclosure includes all the subjects comprising all combinations of the combinable characteristics described in the present specification.

EXAMPLES

The present disclosure is described in more detail with reference to Examples. However, the present disclosure is not limited to the following Examples.
Evaluation Test Methods
Evaluation Tests for Water-Absorbent Resin
Each water-absorbent resin obtained in the following Examples and Comparative Examples was subjected to the following various tests for evaluation. Each test method is described below.
1) Physiological Saline Absorption Capacity
500 g of a 0.9 mass % sodium chloride aqueous solution (physiological saline) was weighed and placed in a 500-mL beaker, and 2.0 g of water-absorbent resin was dispersed in the solution with stirring at 600 r/min so as not to form lumps. Stirring was continued for 60 minutes to allow the water-absorbent resin to swell sufficiently. Thereafter, the contents of the beaker were filtered through a standard sieve (diameter: 200 mm) with an opening of 75 μm whose mass Wa (g) had been measured beforehand. The sieve was then inclined at an angle of about 30 degrees relative to the horizon, and left to stand in this state for 30 minutes so as to filter out excess water. The mass Wb (g) of the sieve containing the swelled gel was measured, and the physiological saline absorption capacity was determined according to the following equation.

Physiological saline absorption capacity (g/g)=[$Wb$−$Wa$](g)/the mass of water-absorbent resin (g)

2) Physiological Saline Retention Capacity
500 g of a 0.9 mass % sodium chloride aqueous solution (physiological saline) was weighed and placed in a 500-mL beaker, and 2.0 g of water-absorbent resin was dispersed in the solution with stirring at 600 r/min so as not to form lumps. Stirring was continued for 30 minutes to allow the water-absorbent resin to swell sufficiently. Thereafter, the swelled gel and physiological saline in the beaker were poured into a cotton bag (cotton broadcloth No. 60, width: 100 nm, height: 200 nm), and the upper part of the cotton bag was tied with a rubber band, followed by dehydration for 1 minute with a dehydrator with the centrifugal force set to 167 G (Kokusan Co., Ltd., Model No.: H-122). The mass Wc (g) of the cotton bag containing the swelled gel after dehydration was measured. The same procedure was performed without adding water-absorbent resin, and the empty mass Wd (g) of the cotton bag that was moistened was measured. Then, the physiological saline retention capacity was determined according to the following equation.

Physiological saline retention capacity (g/g)=[$Wc$−$Wd$](g)/the mass of water-absorbent resin (g)

Figure 1:
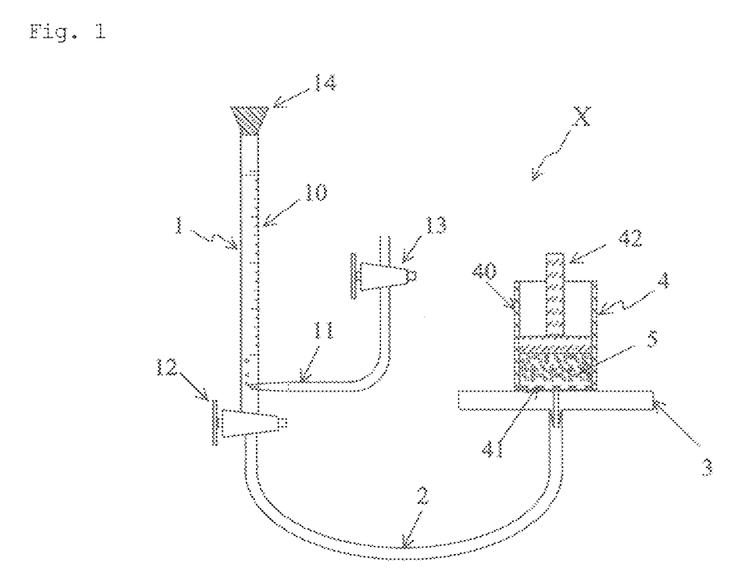
FIG. 1 is a schematic diagram showing the structure of a device X for measuring the physiological saline absorption capacity of a water-absorbent resin under a load of 2.07 kPa.

3) Physiological Saline Absorption Capacity Under a Load of 2.07 kPa
The physiological saline absorption capacity of water-absorbent resin under a load of 2.07 kPa was measured with a measurement device X, whose schematic structure is illustrated in FIG. 1.
The measurement device X illustrated in FIG. 1 includes a burette unit 1, a pipe 2, a measurement table 3, and a measurement unit 4 placed on the measurement table 3. The burette unit 1 includes a burette 10 to the upper part of which a rubber plug 14 is connected, and to the lower part of which an air-inlet tube 11 and a cock 12 are connected, with a cock 13 provided at the upper part of the air-inlet tube 11. The pipe 2 is provided between the burette unit 1 and measurement table 3, and the pipe 2 has a diameter of 6 mm. The measurement table 3 has a hole with a diameter of 2 mm in the middle of it, and the pipe 2 is connected to the hole. The measurement unit 4 includes a cylinder 40, a nylon mesh 41 adhered to the bottom part of the cylinder 40, and a weight 42. The cylinder 40 has an inner diameter of 2.0 cm. The nylon mesh 41 is a 200 mesh (opening: 75 μm). A predetermined amount of a water-absorbent resin 5 is to be homogeneously sprinkled across on the nylon mesh 41. The weight 42 has a diameter of 1.9 cm and a mass of 59.8 g. This weight 42 is placed on the water-absorbent resin 5, and is set to uniformly apply a load of 2.07 kPa on the water-absorbent resin 5.

In the thus-structured measurement device X, the cock 12 and the cock 13 of the burette unit 1 are first plugged, and a 0.9 mass % sodium chloride aqueous solution (physiological saline) adjusted to 25° C. is added through the upper part of the burette 10. After the upper part of the burette is plugged with the rubber plug 14, the cock 12 and the cock 13 of the burette unit 1 are opened. Subsequently, the height of the measurement table 3 is adjusted so that the end of the pipe 2 at the center of the measurement table 3 is level with the air inlet of the air-inlet tube 11.

0.10 g of the water-absorbent resin 5 was homogeneously sprinkled across on the nylon mesh 41 in the cylinder 40, and the weight 42 was placed on the water-absorbent resin 5. The measurement unit 4 was placed so that the center of the measurement unit 4 corresponds to the opening of the pipe at the center of the measurement table 3.

From the point at which the water-absorbent resin 5 started absorbing water, the decrease in the amount of physiological saline in the burette 10 (the amount of physiological saline absorbed by the water-absorbent resin 5) We (mL) was continuously measured. The physiological saline absorption capacity of the water-absorbent resin 5 under a load after 60 minutes from the start of water absorption was determined according to the following equation using the specific gravity of physiological saline of 1.0 (g/mL).

Figure 2:
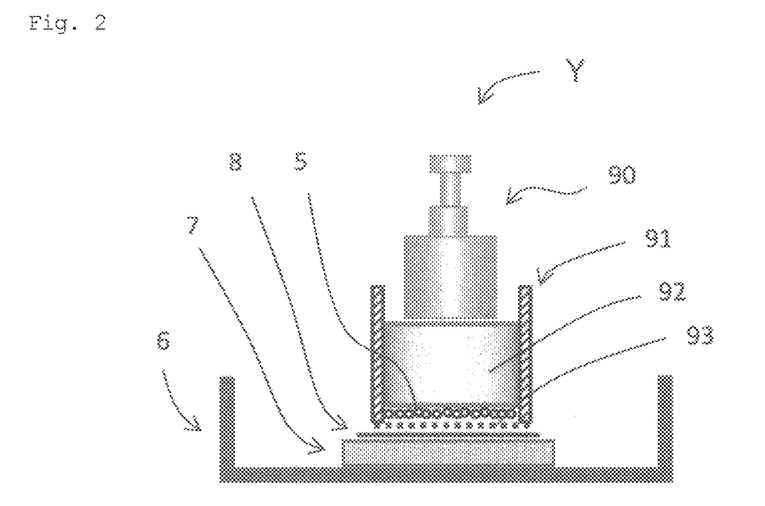
FIG. 2 is a schematic diagram showing the structure of a device Y for measuring the physiological saline absorption capacity of a water-absorbent resin under a load of 4.82 kPa.

Physiological saline absorption capacity under a load of 2.07 kPa (g/g)=$We$ (mL)×1.0 (g/mL)/the mass (g) of water-absorbent resin 4) Physiological Saline Absorption Capacity Under a Load of 4.82 kPa
The physiological saline absorption capacity of the water-absorbent resin under a load of 4.82 kPa was measured with a measurement device Y, whose schematic structure is illustrated in FIG. 2.

The measurement device Y illustrated in FIG. 2 includes a measurement unit, which mainly includes a weight 90, a supporting cylinder 91, and a piston 92; and a liquid supply unit, which mainly includes a Petri dish 6 and a glass filter 7. The measurement unit includes a stainless steel wire mesh 93 (400 mesh, opening: 38 μm) adhered to one side (bottom surface) of the plastic supporting cylinder 91 having an inner diameter of 60 mm. The cylinder includes, on its inside, the piston 92, whose diameter is slightly smaller than 60 mm. The piston 92 is positioned so that no gap is formed between its wall surface and the supporting cylinder 91, and so that its vertical movement is not disturbed. The cylinder also includes, on its inside, the weight 90 above the piston 92. The piston 92 and the weight 90 are capable of applying a uniform load of 4.82 kPa to the water-absorbent resin 5. The thus-structured measurement unit was used, and 0.90 g of the water-absorbent resin 5 was homogeneously spread on the wire mesh in the supporting cylinder 91. Then, the piston 92 and the weight 90 were placed, and the mass Wf (g) of the measurement unit was measured. The mass Wf (g) is the sum of the masses of the supporting cylinder 91, the water-absorbent resin 5, the piston 92, and the weight 90.

Separately, a glass filter 7 (Sibata Scientific Technology Ltd.) with a diameter of 90 mm and a thickness of 5 mm was placed inside the Petri dish 6 with a diameter of 150 mm, and a 0.9 mass % sodium chloride aqueous solution (physiological saline) adjusted to 25±1° C. was added to the Petri dish 6 to the same level as the upper surface of the glass filter 7. Subsequently, a piece of a filter paper 8 (Advantec, No. 2) with a diameter of 9 cm was placed on top of the glass filter 7, and the liquid supply unit was thus prepared. The filter paper 8 was confirmed to be wet over the entire surface, and excess liquid, which may be present, was absorbed with tissue paper as appropriate.

The measurement unit was placed on the liquid supply unit to allow the water-absorbent resin 5 to absorb the physiological saline under a load of 4.82 kPa. When the liquid level of the liquid supply unit was lower than the upper surface of the glass filter 7, physiological saline was added as appropriate to maintain the liquid level constant. Sixty minutes after the measurement unit was placed on the liquid supply unit, the measurement unit was removed from the liquid supply unit, and the mass Wg (g) was measured.

The physiological saline absorption capacity (g/g) under a load of 4.82 kPa was determined according to the following equation.

$$\text{Physiological saline absorption capacity under a load of 4.82 kPa (g/g)} = [Wg - Wf](g)/\text{the mass of water-absorbent resin (g)}$$

5) Dynamic Water Absorption Rate

The dynamic water absorption rate was measured in a room adjusted to 25° C.±1° C. Physiological saline was weighed (50±0.1 g) and placed in a 100-mL beaker, and adjusted to a temperature of 25±0.2° C. in a constant-temperature water tank. Thereafter, stirring was performed with a magnetic stirrer bar (with no ring of 8-mm diameter× 30 mm) to generate a vortex at a rotation frequency of 600 r/min. Then, 2.0±0.002 g of the water-absorbent resin was added at a time into the physiological saline, and the time (sec) from the addition of the water-absorbent resin to the point at which the vortex on the liquid surface disappeared was measured. The measured time was converted into minutes, which was determined to be the dynamic water absorption time (min).

The dynamic water absorption rate (1/min) was calculated as follows.

$$\text{Dynamic water absorption rate}(1/\text{min}) = (\text{the amount of physiological saline/the amount of water-absorbent resin})/(\text{dynamic water absorption time (min)})$$

6) Static Water Absorption Rate

The static water absorption rate of water-absorbent resin was measured with the measurement device X, whose schematic structure is illustrated in FIG. 1, in a manner similar to the measurement described above of the physiological saline absorption capacity under a load of 2.07 kPa, except that the measurement was performed under no load without using the weight 42. In this measurement method, the weight 42 was not used as described above. Accordingly, the water-absorption rate of the water-absorbent resin 5 was measured with no load applied (i.e., under no load).

In the same manner as above, from the point at which the water-absorbent resin 5 under no load started absorbing water, the decrease in the amount of physiological saline in the burette 10 (the amount of physiological saline absorbed by the water-absorbent resin 5) Wi (mL) was continuously measured. Then, the amount of physiological saline absorbed by the water-absorbent resin 5 by a specific time was calculated according to the following equation. The specific gravity of physiological saline was regarded as 1.0 g/mL.

$$\text{Amount of physiological saline absorbed by the water-absorbent resin 5 (g/g)} = Wi \text{ (mL)} \times 1.0 \text{ (g/mL)}/\text{the mass of water-absorbent resin (g)}$$

When the amount of physiological saline absorbed by the water-absorbent resin 5 (g/g) was measured as above, the time (sec) required for the water-absorbent resin 5 to absorb 25 g of physiological saline per 1 g of the water-absorbent resin 5 was measured with a stopwatch as the elapsed time from the point at which the water-absorbent resin 5 started absorbing water. This time was converted to minutes and determined to be the static water absorption time (min). The static water absorption rate (1/min) was calculated according to the following equation.

$$\text{Static water absorption rate}(1/\text{min}) = 25 \text{ (g/g)}/\text{static water absorption time (min)}$$

7) Median Particle Size (Particle Size Distribution)

JIS standard sieves were combined in the following order from the top: a sieve with an opening of 850 μm, a sieve with an opening of 600 μm, a sieve with an opening of 500 μm, a sieve with an opening of 425 μm, a sieve with an opening of 300 μm, a sieve with an opening of 250 μm, a sieve with an opening of 150 μm, and a receiving tray.

50 g of the water-absorbent resin was placed in the top sieve of the combination of the sieves and classified by shaking for 20 minutes using a rotating-tapping shaker (Sieve Factory Iida Co., Ltd.). After classification, the mass of the water-absorbent resin remaining on each sieve was calculated as a mass percentage of the total mass, and the particle size distribution was obtained. Regarding the particle size distribution, the particles on each sieve were integrated in order from the largest particle size, and the correlation between the sieve opening and the cumulative mass percentage of the water-absorbent resin remaining on the sieves was plotted on logarithmic probability paper. The dots on the paper were connected to form a straight line, and the particle size at which the cumulative mass percentage was 50 mass % was determined to be the median particle size.

Evaluation Test of Absorbent Material Comprising Water-Absorbent Resin

8) Amount of Backflow (a) Preparation of Test Liquid 2.5 g of calcium chloride dihydrate, 5.0 g of magnesium chloride hexahydrate, 20 g of potassium chloride, 20 g of sodium sulfate, 8.5 g of ammonium dihydrogen phosphate, 1.5 g of diammonium hydrogen phosphate, and an appropriate amount of distilled water were placed in a 10-L container and completely dissolved. The remaining distilled water was all added for dilution, and the mixture was colored with a small amount of Blue No. 1, thus preparing a test liquid.

(b) Production of Absorbent Material and Absorbent Article 6.6 g of water-absorbent resin and 10 g of crushed pulp (Rayonier Advanced Materials, Rayfloc) were uniformly mixed using an air papermaking technique to produce an absorbent material core with a size of 40 cm×12 cm. Next, the core was pressed entirely by applying a load of 196 kPa for 30 seconds with two sheets of tissue paper of the same size as the absorbent material core and a basis weight of 16 g/m² being placed above and below the absorbent material core, thus producing an absorbent material containing 40 mass % of the water-absorbent resin. Further, an air-through porous liquid-permeable sheet made of polyethylene having the same size as the absorbent material and having a basis weight of 22 g/m² was placed on the upper surface of the absorbent material while a liquid-impermeable sheet made of polyethylene having the same size and having the same basis weight was placed below the absorbent material to sandwich the absorbent material to thus obtain an absorbent article for analysis.

(c) Measurement of Backflow Amount

First, the absorbent article was placed on a horizontal board. A cylinder for liquid injection having an opening with an inner diameter of 3 cm was placed in the center of the absorbent article, and 50 mL of the test liquid was fed into the cylinder at a time. After the test liquid permeated, the cylinder was removed, and the absorbent article was kept as is. The same procedure was performed 30 minutes and 60 minutes after the start of the first injection of the test liquid, using the cylinder in the same position as the first time. Sixty minutes after the third injection of the test liquid, pieces of filter paper (10 cm×10 am) whose mass had been measured in advance (Wk (g), about 70 g) were placed on the absorbent article at the position in which the test liquid was injected so as to cover the center of the absorbent article. Then, a weight having a mass of 5 kg with a bottom surface of 10 cm×10 cm was placed on the filter paper. After the load was applied for 5 minutes, the mass of the filter paper after the test (Wl (g)) was measured, and the increase in mass was calculated using the following equation and determined to be the amount of backflow (g).

Amount of backflow (g)=$Wl-Wk$

EXAMPLES AND COMPARATIVE EXAMPLES

Example 1

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.62 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

78 g (0.87 mol) of a 80 mass % acrylic acid aqueous solution was placed in a 500-mL Erlenmeyer flask, and 120.6 g of a 22.4 mass % sodium hydroxide aqueous solution was added dropwise with cooling from outside to neutralize the mixture. 1.170 g of hydroxyl ethyl cellulose (Sumitomo Seika Chemicals Co., Ltd., HEC AW-15F) as a thickening agent, 0.055 g (0.203 mmol) of potassium persulfate as a radical polymerization initiator, and 59.0 g of ion-exchanged water were added to the mixture and dissolved, thus preparing an monomer aqueous solution with a monomer concentration of 30 mass-. (The monomer concentration refers to the mass ratio of water-soluble ethylenically unsaturated monomers and salts thereof to the total amount of the monomer aqueous solution; in this specification, the same applies below.)

The thus-prepared monomer aqueous solution was added to a separable flask, followed by stirring for 10 minutes. Thereafter, 6.2 g of a surfactant solution in which 0.62 g of sucrose stearate (HLB3, Mitsubishi-Kagaku Foods Corporation, RYOTO Sugar Ester S-370) as a surfactant was dissolved by heating in 5.62 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

After the completion of the first-stage polymerization, the reaction liquid was heated in an oil bath at 125° C. While n-heptane was refluxed by azeotropic distillation of n-heptane and water, 155.3 g of water was removed from the system. Thereafter, 3.90 g (0.45 mmol) of a 2 mass aqueous solution of ethylene glycol diglycidyl ether was added as a post-crosslinking agent, and the mixture was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.2 mass % based on the dry product, and the mixture was passed through a sieve with an opening of 1000 μm, thus obtaining 82.1 g of water-absorbent resin with a median particle size of 350 μm in spherical form. This water-absorbent resin and an absorbent material obtained by using this water-absorbent resin were evaluated in accordance with the various test methods described above.

Example 2

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.52 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

65 g (0.72 mol) of a 80 mass % acrylic acid aqueous solution was placed in a 500-mL Erlenmeyer flask, and 100.5 g of a 22.4 mass % sodium hydroxide aqueous solution was added dropwise with cooling from outside to neutralize the mixture. Then, 0.065 g of hydroxyl ethyl cellulose (Sumitomo Seika Chemicals Co., Ltd., HEC AW-15F) as a thickening agent, 0.046 g (0.170 mmol) of potassium persulfate as a radical polymerization initiator, 0.011 g (0.063 mmol) of ethylene glycol diglycidyl ether as an internal crosslinking agent, and 92.0 g of ion-exchanged water were added to the mixture and dissolved, thus preparing a monomer aqueous solution with a monomer concentration of 25 mass.

The thus-prepared monomer aqueous solution was added to a separable flask, followed by stirring for 10 minutes. Thereafter, 5.2 g of a surfactant solution in which 0.52 g of sucrose stearate (HLB3, Mitsubishi-Kagaku Foods Corporation, RYOTO Sugar Ester S-370) as a surfactant was dissolved by heating in 4.68 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

94.3 g (1.05 mol) of a 80 mass % acrylic acid aqueous solution was placed in another 500-mL Erlenmeyer flask, and 116.2 g of a 28.1 mass % sodium hydroxide aqueous solution was added dropwise with cooling from outside to neutralize the mixture. Then, 0.066 g (0.244 mmol) of potassium persulfate as a radical polymerization initiator, 0.009 g (0.052 mmol) of ethylene glycol diglycidyl ether as an internal crosslinking agent, and 1.9 g of ion-exchanged water were added to the mixture and dissolved, thus preparing a monomer aqueous solution in the second stage with a monomer concentration of 44 mass %.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then inumersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 259.3 g of water was removed from the system. Thereafter, 4.78 g (0.55 mmol) of a 2 masse aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.2 mass % based on the dry product, and the mixture was passed through a sieve with an opening of 1000 μm, thus obtaining 173.3 g of water-absorbent resin with a median particle size of 332 μm in the form of aggregates of spherical particles. This water-absorbent resin and an absorbent material comprising this water-absorbent resin were evaluated in accordance with the various test methods described above.

Example 3

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 nm) as a stirrer was provided. As a hydrocarbon dispersion medium, 300 g of n-heptane was placed in this flask, and 0.62 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

78 g (0.87 mol) of a 80 mass % acrylic acid aqueous solution was placed in a 500-mL Erlenmeyer flask, and 120.6 g of a 22.4 mass % sodium hydroxide aqueous solution was added dropwise with cooling from outside to neutralize the mixture. Then, 0.078 g of hydroxyl ethyl cellulose (Sumitomo Seika Chemicals Co., Ltd., HEC AW-15F) as a thickening agent, 0.055 g (0.203 mmol) of potassium persulfate as a radical polymerization initiator, 0.013 g (0.075 mmol) of ethylene glycol diglycidyl ether as an internal crosslinking agent, and 59.0 g of ion-exchanged water were added to the mixture and dissolved, thus preparing a monomer aqueous solution with a monomer concentration of 30 mass %.

The thus-prepared monomer aqueous solution was added to a separable flask, followed by stirring for 10 minutes. Thereafter, 6.2 g of a surfactant solution in which 0.62 g of sucrose stearate (HLB3, Mitsubishi-Kagaku Foods Corporation, RYOTO Sugar Ester S-370) as a surfactant was dissolved by heating in 5.62 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

110.8 g (1.23 mol) of a 80 mass % acrylic acid aqueous solution was placed in a 500-mL Erlenmeyer flask, and 136.5 g of a 28.1 mass % sodium hydroxide aqueous solution was added dropwise with cooling from outside to neutralize the mixture. Then, 0.078 g (0.289 mmol) of potassium persulfate as a radical polymerization initiator and 0.010 g (0.057 mmol) of ethylene glycol diglycidyl ether as an internal crosslinking agent were added to the mixture and dissolved, thus preparing a monomer aqueous solution in the second stage with a monomer concentration of 44 mass'. After preparation of the monomer aqueous solution in the second stage, polymerization in the second stage was carried out in the same manner as in Example 2.

After the second-stage polymerization, the reaction liquid was heated in an oil bath at 125° C. While n-heptane was refluxed by azeotropic distillation of n-heptane and water, 263.8 g of water was removed from the system. Thereafter, 5.66 g (0.65 mmol) of a 2 masse aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.2 mass % based on the dry product, and the mixture was passed through a sieve with an opening of 1000 μm, thus obtaining 205.5 g of water-absorbent resin with a median particle size of 350 μm in the form of aggregates of spherical particles. This water-absorbent resin and an absorbent material comprising this water-absorbent resin were evaluated in accordance with the various test methods described above.

Example 4

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.74 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

92 g (1.02 mol) of a 80 mass % acrylic acid aqueous solution was placed in a 500-mL Erlenmeyer flask, and 142.3 g of a 22.4 mass % sodium hydroxide aqueous solution was added dropwise with cooling from outside to neutralize the mixture. Then, 0.092 g of hydroxyl ethyl cellulose (Sumitomo Seika Chemicals Co., Ltd., HEC AW-15F) as a thickening agent, 0.064 g (0.237 mmol) of potassium persulfate as a radical polymerization initiator, 0.016 g (0.092 mmol) of ethylene glycol diglycidyl ether as an internal crosslinking agent, and 26.0 g of ion-exchanged water were added to the mixture and dissolved, thus preparing a monomer aqueous solution with a monomer concentration of 35 mass %.

The thus-prepared monomer aqueous solution was added to a separable flask, followed by stirring for 10 minutes. Thereafter, 7.3 g of a surfactant solution in which 0.74 g of sucrose stearate (HLB3, Mitsubishi-Kagaku Foods Corporation, RYOTO Sugar Ester S-370) as a surfactant was dissolved by heating in 6.62 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

128.8 g (1.43 mol) of a 80 mass acrylic acid aqueous solution was placed in another 500-mL Erlenmeyer flask, and 158.8 g of a 28.1 mass % sodium hydroxide aqueous solution was added dropwise with cooling from outside to neutralize the mixture. Then, 0.090 g (0.333 mmol) of potassium persulfate as a radical polymerization initiator and 0.012 g (0.069 mmol) of ethylene glycol diglycidyl ether as an internal crosslinking agent were added to the mixture and dissolved, thus preparing a monomer aqueous solution in the second stage with a monomer concentration of 44 masse.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then immersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 283.6 g of water was removed from the system. Thereafter, 6.62 g (0.76 mmol) of a 2 masse aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.2 mass % based on the dry product, and the mixture was passed through a sieve with an opening of 1000 μm, thus obtaining 230.7 g of water-absorbent resin with a median particle size of 361 μm in the form of aggregates of spherical particles. This water-absorbent resin and an absorbent material comprising this water-absorbent resin were evaluated in accordance with the various test methods described above.

Comparative Example 1

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.74 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

92 g (1.02 mol) of a 80 mass % acrylic acid aqueous solution was placed in a 500-mL Erlenmeyer flask, and 142.5 g of a 21.5 mass % sodium hydroxide aqueous solution was added dropwise with cooling from outside to neutralize the mixture. Then, 0.092 g of hydroxyl ethyl cellulose (Sumitomo Seika Chemicals Co., Ltd., HEC AW-15F) as a thickening agent, 0.064 g (0.237 mmol) of potassium persulfate as a radical polymerization initiator, 0.010 g (0.057 mmol) of ethylene glycol diglycidyl ether as an internal crosslinking agent, and 10.0 g of ion-exchanged water were added to the mixture and dissolved, thus preparing a monomer aqueous solution with a monomer concentration of 37 mass.

The thus-prepared monomer aqueous solution was added to a separable flask, followed by stirring for 10 minutes. Thereafter, 7.4 g of a surfactant solution in which 0.74 g of sucrose stearate (HLB3, Mitsubishi-Kagaku Foods Corporation, RYOTO Sugar Ester S-370) as a surfactant was dissolved by heating in 6.62 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

128.8 g (1.43 mol) of a 80 mass % acrylic acid aqueous solution was placed in another 500-mL Erlenmeyer flask, and 142.5 g of a 27.0 mass % sodium hydroxide aqueous solution was added dropwise with cooling from outside to neutralize 75 mol, of the acrylic acid. Then 0.090 g (0.333 mmol) of potassium persulfate as a radical polymerization initiator and 0.012 g (0.069 mmol) of ethylene glycol diglycidyl ether as an internal crosslinking agent were added to the mixture and dissolved, thus preparing a monomer aqueous solution in the second stage with a monomer concentration of 44 mass-.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then immersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 266.2 g of water was removed from the system. Thereafter, 4.42 g (0.51 mmol) of a 2 masse aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.2 mass % based on the dry product, and the mixture was passed through a sieve with an opening of 1000 μm, thus obtaining 229.7 g of water-absorbent resin with a median particle size of 345 μm in the form of aggregates of spherical particles. This water-absorbent resin and an absorbent material comprising this water-absorbent resin were evaluated in accordance with the various test methods described above.

Comparative Example 2

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 nm) as a stirrer was provided. As a hydrocarbon dispersion medium, 300 g of n-heptane was placed in this flask, and 0.74 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

92 g (1.02 mol) of a 80 mass % the acrylic acid aqueous solution was placed in a 500-mL Erlenmeyer flask, and 142.5 g of a 21.5 mass % sodium hydroxide aqueous solution was added dropwise with cooling from outside to neutralize the mixture. Then, 0.092 g of hydroxyl ethyl cellulose (Sumitomo Seika Chemicals Co., Ltd., HEC AW-15F) as a thickening agent, 0.064 g (0.237 mmol) of potassium persulfate as a radical polymerization initiator, 0.010 g (0.057 mmol) of ethylene glycol diglycidyl ether as an internal crosslinking agent, and 10.0 g of ion-exchanged water were added to the mixture and dissolved, thus preparing a monomer aqueous solution with a monomer concentration of 37 mass %.

The thus-prepared monomer aqueous solution was added to a separable flask, followed by stirring for 10 minutes. Thereafter, 7.4 g of a surfactant solution in which 0.74 g of sucrose stearate (HLB3, Mitsubishi-Kagaku Foods Corporation, RYOTO Sugar Ester S-370) as a surfactant was dissolved by heating in 6.66 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

128.8 g (1.43 mol) of a 80 mass % acrylic acid aqueous solution was placed in another 500-mL Erlenmeyer flask, and 142.5 g of a 27.0 mass % sodium hydroxide aqueous solution was added dropwise with cooling from outside to neutralize 75 mol % of the acrylic acid. Then 0.090 g (0.333 mmol) of potassium persulfate as a radical polymerization initiator and 0.012 g (0.069 mmol) of ethylene glycol diglycidyl ether as an internal crosslinking agent were added to the mixture and dissolved, thus preparing a monomer aqueous solution in the second stage with a monomer concentration of 44 mass %.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then immersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 261.8 g of water was removed from the system. Thereafter, 4.42 g (0.51 mmol) of a 2 masse aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.5 mass % based on the dry product, and the mixture was passed through a sieve with an opening of 1000 μm, thus obtaining 234.2 g of water-absorbent resin with a median particle size of 380 μm in the form of aggregates of spherical particles. This water-absorbent resin and an absorbent material comprising this water-absorbent resin were evaluated in accordance with the various test methods described above.

Comparative Example 3

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.74 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

92 g (1.02 mol) of a 80 mass % the acrylic acid aqueous solution was placed in a 500-mL Erlenmeyer flask, and 142.5 g of a 21.5 mass % sodium hydroxide aqueous solution was added dropwise with cooling from outside to neutralize the mixture. Then, 0.092 g of hydroxyl ethyl cellulose (Sumitomo Seika Chemicals Co., Ltd., HEC AW-15F) as a thickening agent, 0.064 g (0.237 mmol) of potassium persulfate as a radical polymerization initiator, 0.010 g (0.057 mmol) of ethylene glycol diglycidyl ether as an internal crosslinking agent, and 10.0 g of ion-exchanged water were added to the mixture and dissolved, thus preparing a monomer aqueous solution with a monomer concentration of 37 mass %.

The thus-prepared monomer aqueous solution was added to a separable flask, followed by stirring for 10 minutes. Thereafter, 7.4 g of a surfactant solution in which 0.74 g of sucrose stearate (HLB3, Mitsubishi-Kagaku Foods Corporation, RYOTO Sugar Ester S-370) as a surfactant was dissolved by heating in 6.66 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

128.8 g (1.43 mol) of a 80 mass % acrylic acid aqueous solution was placed in another 500-mL Erlenmeyer flask, and 142.5 g of a 27.0 mass % sodium hydroxide aqueous solution was added dropwise with cooling from outside to neutralize 75 mol % of the acrylic acid. Then 0.090 g (0.333 mmol) of potassium persulfate as a radical polymerization initiator and 0.012 g (0.069 mmol) of ethylene glycol diglycidyl ether as an internal crosslinking agent were added to the mixture and dissolved, thus preparing a monomer aqueous solution in the second stage with a monomer concentration of 44 mass %.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then immersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 259.7 g of water was removed from the system. Thereafter, 4.42 g (0.51 mmol) of a 2 mass % aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.5 mass % based on the dry product, and the mixture was passed through a sieve with an opening of 1000 μm, thus obtaining 236.0 g of water-absorbent resin with a median particle size of 356 μm in the form of aggregates of spherical particles. This water-absorbent resin and an absorbent material comprising this water-absorbent resin were evaluated in accordance with the various test methods described above.

Comparative Example 4

A 2-L round-bottom cylindrical separable flask with an inner diameter of 110 mm, equipped with a reflux condenser, a dropping funnel, a nitrogen-gas inlet tube, and stirring blades (two sets of 4 slanted paddle blades with a blade diameter of 50 mm) as a stirrer was provided. As a hydrocarbon dispersion medium, 300 g of n-heptane was placed in this flask, and 0.74 g of maleic anhydride-modified ethylene-propylene copolymer (Mitsui Chemicals, Inc., Hi-WAX 1105A) was added as a polymeric dispersant. The mixture was heated with stirring and dissolved, and then cooled to 50° C.

92 g (1.02 mol) of a 80 mass % the acrylic acid aqueous solution was placed in a 500-mL Erlenmeyer flask, and 142.5 g of a 21.5 mass % sodium hydroxide aqueous solution was added dropwise with cooling from outside to neutralize the mixture. Then, 0.092 g of hydroxyl ethyl cellulose (Sumitomo Seika Chemicals Co., Ltd., HEC AW-15F) as a thickening agent, 0.064 g (0.237 mmol) of potassium persulfate as a radical polymerization initiator, 0.018 g (0.103 mmol) of ethylene glycol diglycidyl ether as an internal crosslinking agent, and 10.0 g of ion-exchanged water were added to the mixture and dissolved, thus preparing a monomer aqueous solution with a monomer concentration of 37 mass %.

The thus-prepared monomer aqueous solution was added to a separable flask, followed by stirring for 10 minutes. Thereafter, 7.4 g of a surfactant solution in which 0.74 g of sucrose stearate (HLB3, Mitsubishi-Kagaku Foods Corporation, RYOTO Sugar Ester S-370) as a surfactant was dissolved by heating in 6.66 g of n-heptane was further added thereto. After the inside of the system was sufficiently replaced with nitrogen while stirring, the flask was immersed in a water bath at 70° C. and heated, followed by polymerization for 60 minutes, thus obtaining a polymerization slurry liquid in the first stage.

128.8 g (1.43 mol) of a 80 mass % acrylic acid aqueous solution was placed in another 500-mL Erlenmeyer flask, and 142.5 g of a 27.0 mass % sodium hydroxide aqueous solution was added dropwise with cooling from outside to neutralize 75 mol % of the acrylic acid. Then 0.090 g (0.333 mmol) of potassium persulfate as a radical polymerization initiator and 0.039 g (0.224 mmol) of ethylene glycol diglycidyl ether as an internal crosslinking agent were added to the mixture and dissolved, thus preparing a monomer aqueous solution in the second stage with a monomer concentration of 44 mass %.

After the inside of the separable flask system was cooled to 27° C., the total amount of the monomer aqueous solution in the second stage was added to the polymerization slurry liquid in the first stage. The inside of the system was sufficiently replaced with nitrogen. The flask was then immersed in a water bath at 70° C. again and heated, followed by polymerization in the second stage for 30 minutes.

After the second-stage polymerization, the reaction liquid was heated in an oil bath at 125° C. While n-heptane was refluxed by azeotropic distillation of n-heptane and water, 260.8 g of water was removed from the system. Thereafter, 6.62 g (0.76 mmol) of a 2 mass % aqueous solution of ethylene glycol diglycidyl ether was added as a post-crosslinking agent, and the reaction solution was maintained at 80° C. for 2 hours. Then, n-heptane was evaporated to dryness to thus obtain a dry product. The dry product was mixed with amorphous silica (Evonik Degussa Japan Co., Ltd., Carplex #80) in an amount of 0.5 mass % based on the dry product, and the mixture was passed through a sieve with an opening of 1000 μm, thus obtaining 235.1 g of water-absorbent resin with a median particle size of 343 μm in the form of aggregates of spherical particles. This water-absorbent resin and an absorbent material comprising this water-absorbent resin were evaluated in accordance with the various test methods described above.

Evaluation Results

Evaluation Results of Water-Absorbent Resin and Absorbent Material

Table 1 below shows the evaluation test results for the water-absorbent resin. Table 2 below shows the dry-up index, the overall absorption capacity term α, and the water absorption rate term β of the water-absorbent resin, as well as the evaluation results of the absorbent material comprising the water-absorbent resin (the amount of backflow).

$$\text{Dry-up index} = \text{overall absorption capacity term } \alpha \times \text{water absorption rate term } \beta \quad (1)$$

The overall absorption capacity term α and the water absorption rate term β are determined according to the following equations (2) and (3).

$$\text{Overall absorption capacity term } \alpha = \frac{\left(\begin{array}{c}\text{physiological saline absorption}\\\text{capacity under a load of 2.07 kPa} -\\\text{physiological saline absorption}\\\text{capacity under a load of 4.82 kPa}\end{array}\right)}{\left(\begin{array}{c}\text{physiological saline absorption capacity} -\\\text{physiological saline retention capacity}\end{array}\right)} \quad (2)$$

$$\text{Water absorption rate term } \beta = \text{dynamic water absorption rate/static water absorption rate} \quad (3)$$

TABLE 1

|  | Physiological saline absorption capacity g/g | Physiological saline retention capacity g/g | Physiological saline absorption capacity under a load of 2.07 kPa g/g | Physiological saline absorption capacity under a load of 4.82 kPa g/g | Dynamic water absorption rate 1/min | Static water absorption rate 1/min |
|---|---|---|---|---|---|---|
| Ex. 1 | 62 | 45 | 30.2 | 11.1 | 9.3 | 4.8 |
| Ex. 2 | 62 | 47 | 34.9 | 12.0 | 23.1 | 13.4 |
| Ex. 3 | 65 | 50 | 31.4 | 11.5 | 23.4 | 13.9 |

TABLE 1-continued

| | Physiological saline absorption capacity g/g | Physiological saline retention capacity g/g | Physiological saline absorption capacity under a load of 2.07 kPa g/g | Physiological saline absorption capacity under a load of 4.82 kPa g/g | Dynamic water absorption rate 1/min | Static water absorption rate 1/min |
|---|---|---|---|---|---|---|
| Ex. 4 | 64 | 48 | 28.5 | 10.9 | 29.4 | 10.9 |
| Comp. Ex. 1 | 70 | 51 | 14.0 | 7.8 | 30.0 | 11.2 |
| Comp. Ex. 2 | 65 | 45 | 29.0 | 10.5 | 37.5 | 24.2 |
| Comp. Ex. 3 | 63 | 41 | 33.0 | 11.0 | 44.1 | 29.3 |
| Comp. Ex. 4 | 52 | 31 | 31.4 | 22.0 | 40.5 | 30.0 |

TABLE 2

| | Overall absorption capacity term α — | Water absorption rate term β — | Dry-up index — | Amount of backflow in absorbent material g |
|---|---|---|---|---|
| Ex. 1 | 1.12 | 1.93 | 2.17 | 18.2 |
| Ex. 2 | 1.53 | 1.72 | 2.63 | 22.5 |
| Ex. 3 | 1.33 | 1.69 | 2.24 | 23.2 |
| Ex. 4 | 1.10 | 2.69 | 2.95 | 25.5 |
| Comp. Ex. 1 | 0.33 | 2.68 | 0.87 | 34.8 |
| Comp. Ex. 2 | 0.93 | 1.55 | 1.43 | 32.8 |
| Comp. Ex. 3 | 1.00 | 1.51 | 1.51 | 35.0 |
| Comp. Ex. 4 | 0.45 | 1.35 | 0.60 | 40.3 |

DESCRIPTION OF THE REFERENCE NUMERALS 1 burette unit
10 burette
11 air-inlet pipe
12 cock
13 cock
14 rubber plug
2 pipe
3 measurement table
4 measurement unit
40 cylinder
41 nylon mesh
42 weight
5 water-absorbent resin particles
6 Petri dish
7 glass filter
8 filter paper
90 weight
91 plastic supporting cylinder
92 piston
93 stainless steel wire mesh
X measurement device
Y measurement device

The invention claimed is:

1. A water-absorbent resin that is a crosslinked polymer of a water-soluble ethylenically unsaturated monomer, the water-absorbent resin having a dry-up index of 2.2 or more, the dry-up index being represented by the following equation (1):

$$\text{dry-up index} = \text{overall absorption capacity term } \alpha \times \text{water absorption rate term } \beta \quad (1),$$

wherein the overall absorption capacity term α and the water absorption rate term β are determined according to the following equations (2) and (3):

overall absorption capacity term α =

$$\text{overall absorption capacity term } \alpha = \frac{\left(\begin{array}{c}\text{physiological saline absorption}\\\text{capacity under a load of 2.07 kPa} -\\\text{physiological saline absorption}\\\text{capacity under a load of 4.82 kPa}\end{array}\right)}{\left(\begin{array}{c}\text{physiological saline absorption capacity} -\\\text{physiological saline retention capacity}\end{array}\right)}; \quad (2)$$

water absorption rate term β = dynamic water absorption rate/static water absorption rate (3), wherein the degree of neutralization of the water-soluble ethylenically unsaturated monomer is 77 to 80 mol % of all acid groups in the water-soluble ethylenically unsaturated monomer,
the water-soluble ethylenically unsaturated monomer is (meth)acrylic acid,
the overall absorption capacity term α is 0.95 or more,
the water absorption rate term β is 1.56 or more, and
the water-absorbent resin is prepared by a polymerization method satisfying all of conditions (i), (ii), and (iii):
(i) the molar ratio of a water-soluble ethylenically unsaturated monomer and an internal crosslinking agent used in polymerization in the first stage (water-soluble ethylenically unsaturated monomer/internal crosslinking agent) is $10 \times 10^3$ to $15 \times 10^3$;
(ii) the molar ratio of a water-soluble ethylenically unsaturated monomer and an internal crosslinking agent used in polymerization in the second stage (water-soluble ethylenically unsaturated monomer/internal crosslinking agent) is $15 \times 10^3$ to $25 \times 10^3$;
(iii) the molar ratio of the total amount of water-soluble ethylenically unsaturated monomer used in polymerization in which a resin used in a post-crosslinking reaction is prepared and a post-crosslinking agent (water-soluble ethylenically unsaturated monomer/post-crosslinking agent) is $2.5 \times 10^3$ to $4.5 \times 10^3$.

2. The water-absorbent resin according to claim 1, wherein the difference between the physiological saline absorption capacity and the physiological saline retention capacity is 18 or less.

3. The water-absorbent resin according to claim 1, wherein the difference between the physiological saline absorption capacity under a load of 2.07 kPa and the physiological saline absorption capacity under a load of 4.82 kPa is 17 to 36.

4. The water-absorbent resin according to claim 1, wherein the internal crosslinking agent is at least one member selected from the group consisting of (poly)ethylene glycol diglycidyl ether, (poly)propylene glycol diglycidyl ether, and (poly)glycerol diglycidyl ether.

5. The water-absorbent resin according to claim 1, wherein the post-crosslinking agent is at least one member selected from the group consisting of (poly)ethylene glycol diglycidyl ether, (poly)propylene glycol diglycidyl ether, and (poly)glycerol diglycidyl ether.

6. The water-absorbent resin according to claim 1,
wherein the internal crosslinking agent is at least one member selected from the group consisting of (poly)ethylene glycol diglycidyl ether, (poly)propylene glycol diglycidyl ether, and (poly)glycerol diglycidyl ether, and the post-crosslinking agent is at least one member selected from the group consisting of (poly)ethylene glycol diglycidyl ether, (poly)propylene glycol diglycidyl ether, and (poly)glycerol diglycidyl ether.

7. An absorbent material comprising 5 to 50 mass % of the water-absorbent resin according to claim 1.

* * * * *